United States Patent [19]

Evans

[11] Patent Number: 5,078,486

[45] Date of Patent: Jan. 7, 1992

[54] SELF-CALIBRATING VISION TEST APPARATUS

[76] Inventor: David W. Evans, 4015 Gateway Rd., Englewood, Ohio 45322

[21] Appl. No.: 421,535

[22] Filed: Oct. 13, 1989

[51] Int. Cl.$^5$ .............................................. A61B 3/02
[52] U.S. Cl. ..................................... 351/243; 351/203
[58] Field of Search ............... 351/203, 243, 221, 200; 358/161, 168, 139

[56] References Cited

U.S. PATENT DOCUMENTS 4,415,921  11/1983  Mulvanny et al. ................... 358/139
4,514,727  4/1985  Van Antwerp ....................... 358/161

OTHER PUBLICATIONS

The Journal of the American Academy of Ophthalmogy, Aug. 24, 1989, p. 99.

Primary Examiner—Paul M. Dzierzynski
Attorney, Agent, or Firm—Wood, Herron & Evans

[57] ABSTRACT

A vision test apparatus illuminated by internal light source generating a constant, predetermined light intensity in the vicinity of the eye chart. The unit employs at least one photocell to monitor the light intensity near the eye chart and thereby adjust the amount of light generated by the light source to provide a constant level of illumination near the eye chart.

25 Claims, 3 Drawing Sheets

5,078,486

SELF-CALIBRATING VISION TEST APPARATUS

FIELD OF THE INVENTION

This invention relates to a vision testing unit having a face illuminated from the rear for presenting various vision test charts.

BACKGROUND OF THE INVENTION

Vision testing using eye charts has long been used in evaluating an individual's vision. Early charts were printed on paper or other like material, displayed vertically on a wall or other support and illuminated by the ambient light within the room. Because the light in the room was produced primarily by the sun, the light intensity varied significantly with the season and the weather conditions. In turn, since the human eye perceives shapes better under increased lighting conditions, it can be appreciated that variations in the amount of light illuminating the eye chart would have a significant effect on the eye test results.

In the early testing rooms, the light striking the eye chart was dependent on both the light provided from within the room as well as sunlight entering from outside the room. To decrease the variation in illumination, testing rooms were made windowless to allow only the artificial light to illuminate the eye chart. This light was more controllable by the tester, and thus served to decrease variability and thereby improve the reproducibility of results over time. An alternative method of conducting the vision test was to print the test onto translucent glass and provide illumination from behind.

Though illumination of the test chart by the use of only artificial light improved the reproducibility of the test method, variations still existed. The light bulbs used to create the artificial light did not produce a uniform light output. As the bulbs aged, their output intensity varied. This non-linear output hampered the efforts of eye testers to compare test results obtained over a period of time.

One device which attempted to address the illumination variation problem was produced by Vistech Consultants, Inc. A prototype unit was introduced in 1985, and was ultimately designated the MCT-8000. The unit provided front lighting onto an eye chart surface and had a photocell located adjacent to the light bulb for detecting the bulb output. The photocell was connected to a readout device. The readout was manually compared to factory-determined light intensity values which would correspond to day- and night-time lighting conditions.

SUMMARY OF THE INVENTION

The invention addresses this non-linear output problem and relates to a vision test unit which automatically compensates for variation of the illuminating light source over time to thereby further improve the reproducibility of the vision testing method. Specifically, the test unit employs a light sensor such as a photocell, in combination with the light source to adjust the light intensity both in response to the ambient light in the room as well as to the output characteristics of the light source itself. In a preferred version of the invention, the unit consists of a single main enclosure which provides back lit illumination to a light transmitting face, thereby permitting use of interchangeable light transmitting eye charts which are affixed to the face.

It is an object of the invention to provide a vision test unit which provides a constant level of illumination on the eye chart over time.

It is a further object to provide a vision test unit which can adjust the amount of internally generated light detected at an eye chart in response to the ambient light level in the vicinity of the vision test unit.

It is a further object to provide a vision test unit which permits the use of interchangeable eye chart sheets.

It is yet a further object of the invention to provide a vision test unit which is portable and able to be set up quickly for testing.

These and other objects and advantages of the invention will be further discussed in the following detailed description and in the drawings, in which:

DETAILED DESCRIPTION OF THE INVENTION

Figure 1:
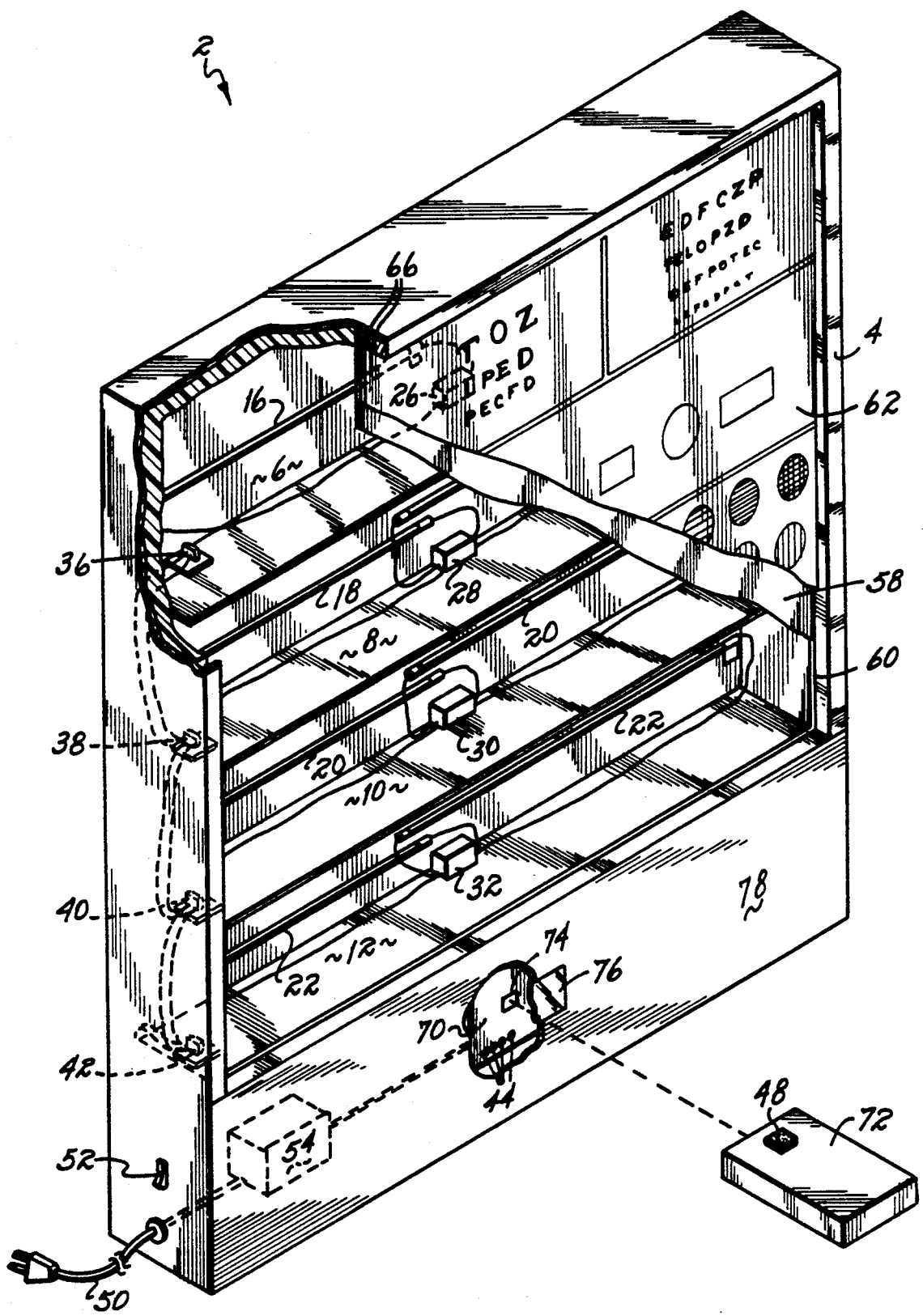
FIG. 1 is a front perspective view of the vision test unit.

The invention in its broader aspects relates to a light generating unit for conducting vision testing comprising an enclosure having at least one chamber with a face capable of transmitting light, an adjustable intensity light source within the chamber, light sensing means, and control means connected to the light source and the light sensing means to provide an electrical energy input to the light source in response to the light intensity in the vicinity of the light sensing means. Preferably, the electrical energy input from the control means varies in direct relation to comparison of the photocell voltage with a reference voltage. As described hereinbelow, the control means is a variable power source, but may be any device which adjusts the electrical energy input to the light source, such as variable current or voltage devices, or the like. It is preferred that the reference voltage itself be adjustable to thereby permit adjustment of the output light intensity.

Where one photocell only is used in the light generating unit, it would be positioned outside the chamber in the vicinity of the face to be able to detect both the light generated from within the unit as well as the ambient light outside the unit. As used herein, the term "vicinity" denotes a distance inside which the photocell is positioned to provide an accurate measurement of light intensity at the face of the unit. For example, the photocell can be adjacent either side of the face, or can be located several inches away on a support arm connected to the unit to minimize interference from other light sources. Alternatively, where the unit is located in a darkened room with no illumination other than that provided by the unit, the photocell can be located a substantial distance away, on the order of several feet or more, with no adverse effect.

A preferred example of a light sensing means is a photocell. Preferably, more than one photocell is used. The photocells are positioned so that one is in the chamber near the light source, with at least one additional photocell able to respond to the intensity of the ambient light in the vicinity of the eye chart distinct from the contribution of the light source.

In an especially preferred version, the unit consists of several chambers, substantially independent of each other, sharing a common light transmitting face. Within each chamber is a photocell and a light source. The multiple chambers illuminate removable eye charts which, for example, have test segments which match the opening size of the individual chambers. Within each chamber are also located photocells which measure the amount of light in the chamber contributed by both the light source and ambient light passing through the light transmitting face from outside the enclosure.

The light source is preferably at least one fluorescent bulb. The intensity of the light source, which provides substantially uniform illumination over the length of the chamber, varies directly with the voltage powering the bulb. The voltage generated by the individual photocells varies inversely with the voltage received by the light source. Thus, where the photocells sense higher levels of illumination, the resultant photocell voltage results in a decreased voltage to the light source which thereby dims the bulb. Also, as the bulb ages, its light output may increase or decrease depending upon the individual characteristics of the bulb itself. The photocell in the same chamber with the bulb senses the light intensity, and as above, adjusts the input voltage to the light source.

One feature of the invention relates to the ability to back illuminate individual chambers of the vision test unit by remote control. It is preferred that the test unit have a switching circuit which, on application of an input signal, cycles the voltage input either to individual chambers or to a complete "off" function. In operation, by successively activating a remote control unit, such as one transmitting infrared radiation, the topmost chamber light source is turned on, followed successively by lower chambers, after which the next input signal causes the light sources in each of the chambers to remain unlighted. Alternatively, a more complex remote transmitter/receiver unit may be employed, which would allow the tester to illuminate individual or multiple chambers at random. The eye tests presently utilized with this invention require only one chamber to be lit at any time, but it is envisioned that tests may be employed which require more than one chamber to be lit simultaneously. However, these tests would require modification of the method of calibrating and operating the preferred version of the test unit, as discussed below.

In the preferred embodiment the enclosure has a light transmitting face upon which an eye test chart is positioned for conducting vision testing. However, this invention is also intended to encompass systems which project the eye test onto a screen removed from the light-generating enclosure. In the projection system, the enclosure contains a light source which is transmitted across a face through a piece of film, or the like, to form a projection of the film's contents onto the screen. The face may be a clear glass plate or the like, which is mounted to the enclosure, or may be merely the film backing on the strip bearing the eye chart contents. This system, having control means and at least one photocell, would allow automatic adjustment of the intensity of the light source within the projector.

In FIG. 1, the vision test unit 2 is comprised of an enclosure 4 which houses chambers 6, 8, 10, and 12. The chambers are constructed of light colored or white light reflecting material such as acrylonitrile-butadiene-styrene terpolymer (ABS). The enclosure is preferably manufactured from black ABS. Within the respective chambers 6, 8, 10, 12 are light sources 16, 18, 20 and 22. In FIG. 1, the light sources 16, 18, 20, 22 are comprised of a pair of miniature fluorescent bulbs, distributed in the United States by JKL Components, Pacoima, Calif., Part No. BF 65262. The bulbs emit a white light which can be dimmed to a specific light level in response to a variable dc signal applied across plus and minus input terminals of respective bulb power supplies 26, 28, 30 and 32 each of which may suitably comprise an AC/DC inverter such as Model No. CXA-L10L available from TDK USA Corp. CEL Division, Indianapolis, Ind., which accepts a 12 volt DC input and provides an output in the range of 600-900 volts AC at an amperage in the range of 7-10 mA. The light sources may alternatively be single bulbs, or series of constant output bulbs, either fluorescent or incandescent, which are sequentially energized as more light is needed.

The light intensity within each of the chambers 6, 8, 10 and 12 is measured by respective photocells 36, 38, 40 and 42 the outputs of which are summed and applied to a reference resistor R7 the inverting output of an op amp configured as a difference amplifier. The photocells 36, 38, 40, 42 preferably contain a cadmium sulfide sensor. The photocells, which are preferably positioned within each of the chambers 6, 8, 10, 12, may each suitably comprise Part No. CL7P5 HL available from Clairex Electronics, Mount Vernon, N.Y. and which is sensitive to light ranging in wavelengths from about 380 to about 700 nanometers (nm), which is similar to the sensitivity range of the human eye. Thus, only that visible light emitted from the bulbs and that contributed by the ambient light outside the chambers serves as the basis for determining the amount of current received by the specific light source. Less desirable photocells respond also to radiation wavelengths not visible by the human eye, such as infrared radiation. It can be seen that a photocell which responds to infrared radiation would adjust the output level of the light source in response to both the heat energy and light energy of the source. Thus, a test unit having such less desirable photocell would produce a variation in visible light output the longer the unit is in operation due in part to the amounts of heat produced by the light source with time.

Face 58 overlies the open fronts of chambers 6, 8, 10, 12. The face 58 is comprised of a light transmitting material such as extruded high molecular weight translucent acrylic white sheet and is secured by inserting the edges into groove 60. For testing purposes, the eye chart 62 is affixed over the face 58. The eye chart 62 is comprised of a light transmitting material such as translucent styrene, and is secured to the face 58 by magnetic strips 66 which permit easy removal of the eye chart 62. Alternatively, the eye chart may be secured by adhesive strips, hooks, or other securing devices.

Though less preferred, it is still considered to be within the spirit of the invention to combine the face and eye chart onto a single sheet from which the eye test is conducted.

To facilitate the switching of power to individual chambers, a switching device 70 is provided and is preferably actuated by a remote control transmitter 72. In the test unit 2 as shown, the transmitter 72 is a MRD 81 infrared hand-held transmitter manufactured by Motorola. The receiving portion is a photodiode 74, specifically an MRD 821 photodiode from Motorola. This remote control system operates on infrared radiation. Advantageously, the photodiode can alternatively be activated by a flashlight or other bright light to switch the power to discrete light sources 16, 18, 20, 22 even if the transmitter 72 is broken or lost. The photodiode 74 is protected from dust and contaminants by the radiation transmitting window 76, which is secured onto plate 78 which overlies the transformer 54, switching circuitry and photodiode 74.

Figure 2:
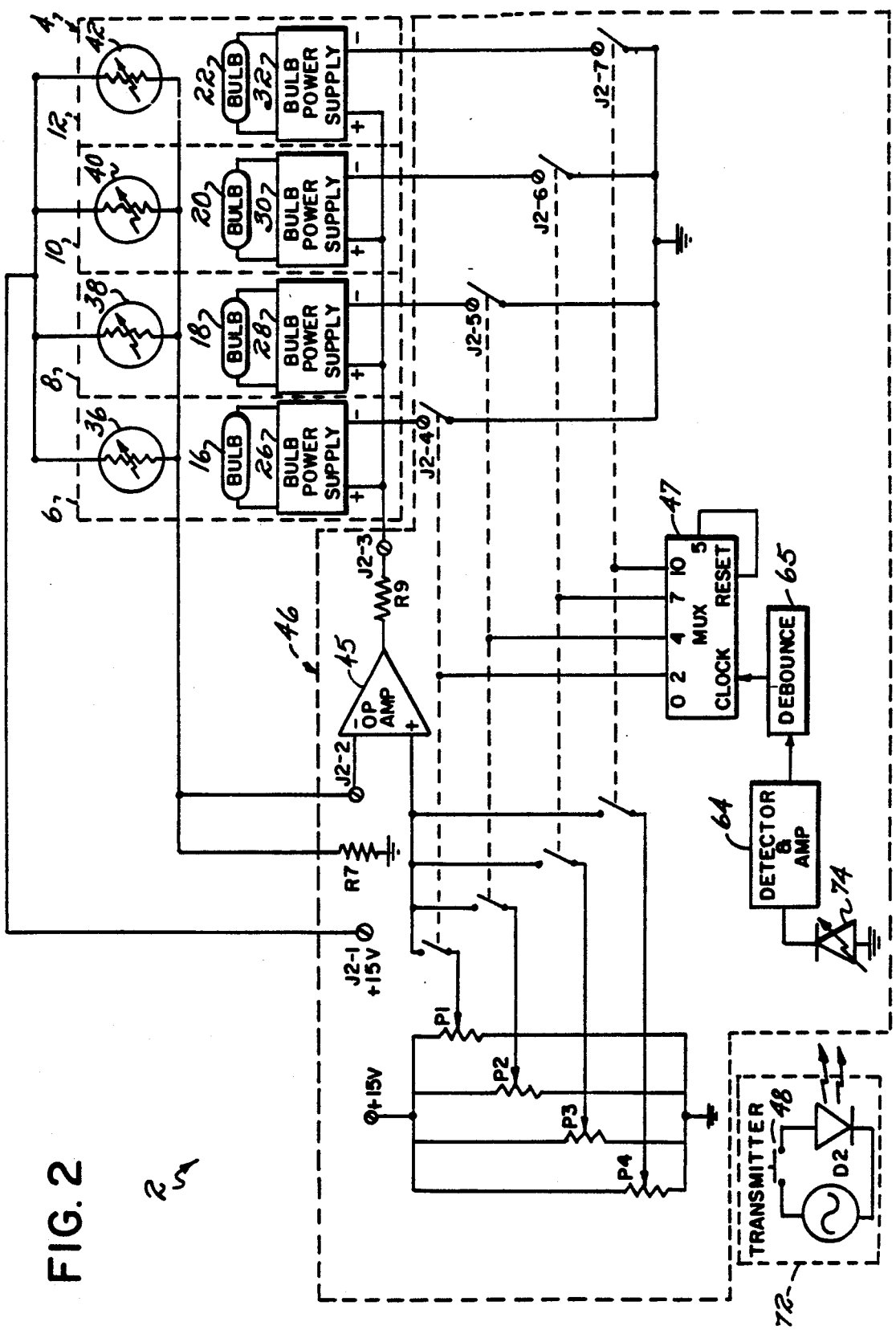
FIG. 2 is a schematic diagram illustrating the illumination control system of the vision test unit of FIG. 1.
Figure 3:
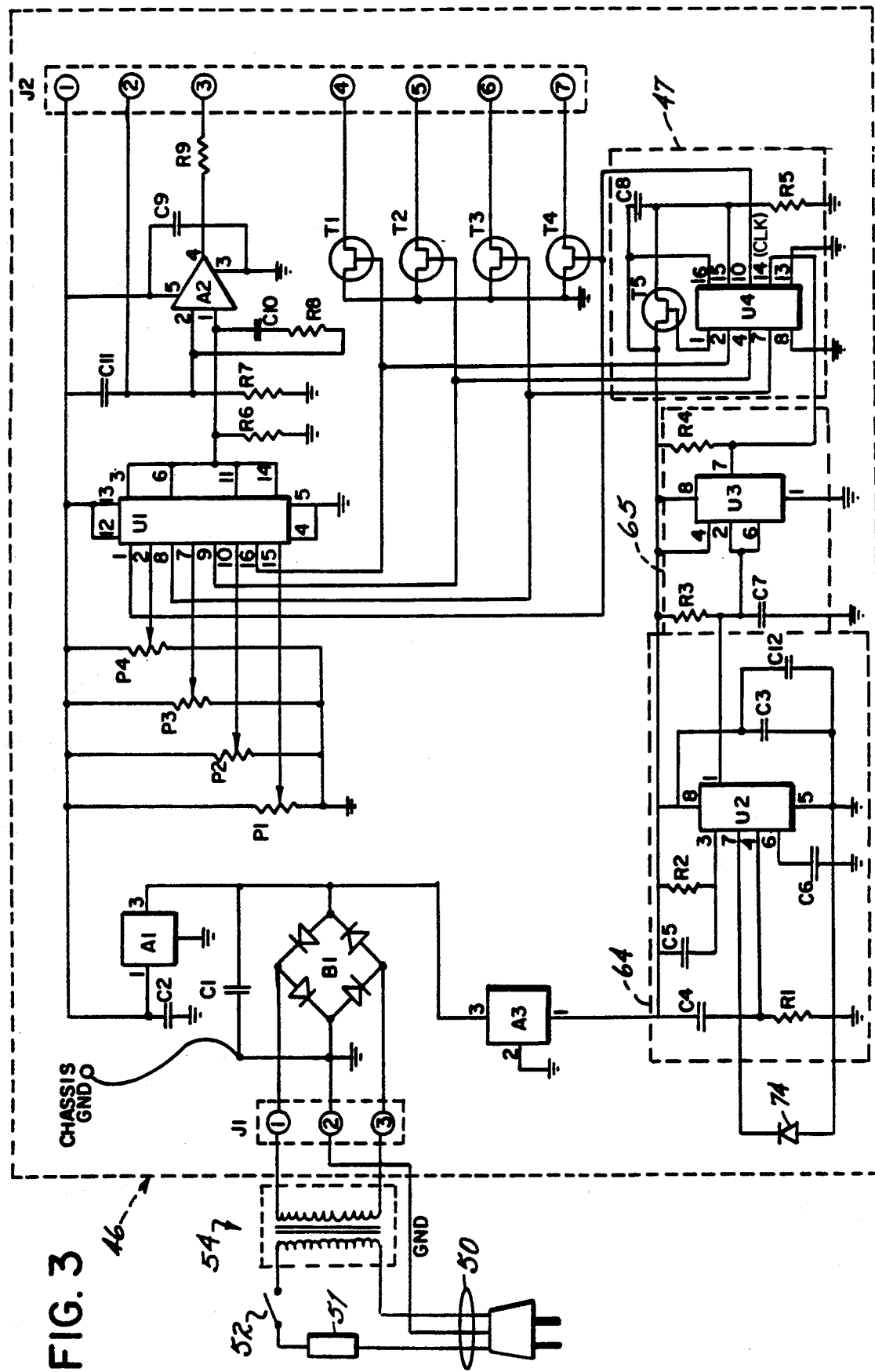
FIG. 3 is an electrical schematic diagram illustrating a preferred construction of the main circuit board of the illumination control of FIG. 2 and the electrical power input connections to same.

Referring to FIGS. 2 and 3, op amp 45 resides on a control circuit board 46 which includes a series of reference potentiometers P1, P2, P3 and P4, the wipers of which may be selectively switched to the non-inverting terminal of op amp 45 under the control of a multiplexer (mux) 47. A parts list for circuit bard 46 is included in Appendix 1. In response to successive signals received at its CLOCK pin, mux 47 sequentially strobes a switching network to connect one of the reference potentiometers P1-P4 to the non-inverting terminal of op amp 45 while simultaneously connecting the reference input of a corresponding one of the bulb power supplies 26, 28, 30 or 32 to ground so that the corresponding bulb 16, 18, 20 or 22 is illuminated to a light level determined by the difference between the voltage developed across R7 by photocells 36, 38, 40 and 42 and the settable voltage applied to the non-inverting terminal of op amp 45 from one of the reference potentiometers P1 or P2 or P3 or P4 each of which is connected between the upper supply voltage and ground.

In order that a user may select which one of the bulbs 16, 18, 20 or 22 is illuminated at any given time, a portable transmitter 72 having an infrared emitting diode, D2 connectable to a power source by way of a user-operated, normally open pushbutton 48 is provided. Pulses from D2 are received by detector diode 74 associated with test unit 2 and preferably mounted on circuit board 46. The output of diode 74 is applied to the CLOCK pin of mux 47 after processing by a detector and amplifier (amp) circuit 64 and a debounce circuit 65.

The control circuit board 46 as well as the electrical power input connections thereto will be described now with additional reference to FIG. 3. Test unit 2 is powered by connecting a power cord 50 to an ordinary 120 volt AC source. Power is routed by way of a line fuse 51 to a step down transformer 54 through a switch 52 which preferably includes a light (not shown) to indicate when test unit 2 is energized.

Transformer 54 is connected across the input of a rectifier bridge B1 by way of terminals J1-1 and J1-3 of a terminal block J1 mounted on circuit board 46. The ground line (GND) of power cord 50 is connected to the chassis of test unit 2 by way of terminal J1-2 as well as to one side of the output of a rectifier bridge B1, whose other output is applied to 15 volt regulator A1 as well as to a 5 volt regulator A3.

Regulator A3 supplies power to detector and amplifier circuit 64 which includes remote control amplifier detector U2 connected to diode 74 and associated resistors and capacitors as shown. The output of U2 at pin #1 thereof is connected to debounce circuit 65 also powered by A3 and which may suitably comprise a monostable multivibrator formed using a type NE555 timer, U3, connected to associated resistors and capacitors as shown.

Multiplexer (mux) 47, which is also powered by regulator A3 may suitably comprise a decimal counter, U4, connected as a four bit ring counter with power-up reset being facilitated by field effect transistor (FET) T5 together with C8 and R5 connected as shown in FIG. 3. In response to successive pulses received at the CLOCK pin of mux 47 (i e., pin #14 of U4), U4 sequentially pulls one of the terminals J2-4, J2-5, J2-6 or J2-7 of a second terminal strip J2 on circuit board 46 to a voltage very near ground. This is carried out by causing a respective one of a series of FETs, T1 or T2 or T3 or T4 to conduct in response to high voltages appearing at either pin numbers 2, 4, 7 or 10 of U4 in accordance with the present count thereof. Pins J2-4, J2-5, J2-6 and J2-7 are connected by wiring (not shown in FIG. 3) to the respective minus reference inputs of corresponding ones of bulb power supplies 26, 28, 30 and 32 as shown in FIG. 2. It should be noted that for the sake of simplicity FETs T1-T4 are schematically represented in FIG. 1 by the series of switches connected to the minus reference input of each bulb power supply.

A second regulator, A1, supplies voltage to potentiometers P1, P2, P3 and P4 as well as to a analog switching device U1. When a logical high voltage appears on pin #10 of U4, and therefore at the gate of FET T4, U1 operates to electrically connect the wiper of potentiometer P4, which is connected to pin #2 of U1, to the common connection which couples pin #s 3, 6, 11 and 14 of U1 to the non-inverting terminal of op amp 45. Similarly, pin #s 8, 9 and 16 of U1 are connected to the output pin #s 7, 4 and 2, respectively, of U4 as well as to the gates of FETs T3, T2 and T1, respectively. Thus, in response to a logical high voltage appearing at pine #10 or pin #7 or pin #4 or pin #2 of U4, the wipers of potentiometers P4 or P3 or P2 or P1, respectively, are coupled one at a time to the non-inverting terminal of op amp 45 at the same time the minus reference input of a corresponding one of the bulb power supplies 32 or 30 or 28 or 26 is pulled near ground by virtue of its connection to T4, T3, T2 or T1 by way of terminals J2-7, J2-6, J2-5 and J2-4, respectively.

The inverting terminal of op amp 45 is connected at terminal J2-2 to a point in common with the output side of photocells 36, 38, 40 and 42 as well as one end of reference resistor R6, the other end of which is grounded. Power is supplied to op amp 45 from regulator A1 which also supplies power to photocells 36, 38, 40 and 42 by way of terminal J2-1. The output of op amp 45 is connected by way of resistor R9 and terminal J2-3 to the commonly connected plus input terminals of bulb power supplies 26, 28, 30 and 32 so that when the minus reference input of one of said power supplies is grounded, the corresponding bulb 16, 18, 20 or 22 will be illuminated with an AC voltage whose magnitude is determined by the DC voltage appearing between the plus and minus reference terminals of the corresponding bulb power supply 16, 18, 20 or 22. That DC voltage is in turn determined in accordance with the voltage difference between the voltage at the non-inverting terminal of op amp 45 and the voltage at the inverting terminal of op amp 45. The former voltage depends on the combined output voltage of photocells 36, 38, 40 and 42 appearing across R7 while the latter depends on the setting of the potentiometer P4, P3, P2 or P1 associated with whichever of bulbs 36, 38, 40 or 42 is lighted.

In operation, the photocells 36-42 generate a voltage across R7 in response to the sensed light intensity. The individual voltages are summed and compared to a reference voltage for the specific chamber established by one of the potentiometers P1-P4, which are each preferably set to correspond to a light intensity of 85 candelas per square meter. The difference between voltage across R7 and reference voltage determines the amount of current sent to the specific light source 16, 18, 20 or 22 to provide the desired amount of light at the face of the unit. In normal operation, the reference voltage set by potentiometers P1-P4 is the same for all light sources and corresponds to a light level of 85 cd/m². However, in certain instances, such as where unit 2 is modified to permit two or more chambers to be lit simultaneously, the reference voltage for those chambers must be adjusted. Adjustment of potentiometers P1-P4 for individual chambers is made at adjustment screws 44, as shown in FIG. 1. In an alternative embodiment, the light output from the chambers 6, 8, 10 and 12 is monitored by a single photocell mounted outside the chambers. This photocell generates a voltage based on the ambient light and the output from one or more energized light sources 16, 18, 20 and 22, and the voltage is then compared to the reference voltage.

The eye chart 62 is preferably divided into four sections running from left to right along the chart 62, each section having a different type of eye test printed thereon. For example, the top portion of the eye chart may have printed thereon a Snellen high contrast letter recognition test. The section below may have a contrast sensitivity test printed thereon, and so on. Preferably, only one chamber is lit at any one time to allow the individual taking the eye test to concentrate on a specific test. When one test has been completed, the individual may be asked to perform another test, located on the eye chart in front of a separate chamber.

The unit as thus described may be employed to provide a variety of vision tests under a range of illumination conditions. The unit is lightweight and portable, permitting easy transport and set up for use in the offices of eye care specialists as well as in schools, nursing homes, community centers, and other remote locations. Where the ambient illumination causes the photocell array to produce a voltage which exceeds the reference voltage corresponding to the desired light level, typically 85 cd/m², the individual light sources will remain unlit. To standardize the test to the preset light level, the ambient illumination must be decreased to allow some contribution by the unit's light sources.

Thus, it is apparent that there has been provided, in accordance with the invention, a vision test unit that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

APPENDIX 1

| Item | Part # | Available From |
|---|---|---|
| B1 | MB11A01V05 | Powerex, Inc. Youngwood, PA |
| J1 | 22-03-2031 | Molex, Lisle, IL |
| J2 | 22-03-2071 | Molex |
| A1 | MC78T15CT | Motorola, Inc. Dayton, OH |
| A2 | LM675T | National Semiconductor Corp. Santa Clara, CA |
| Op Amp 45 | MC78L05ACP | Motorola |
| U1 | DG212CJ | Siliconix, Inc. Santa Clara, CA |

APPENDIX 1-continued

| Item | Part # | Available From |
|---|---|---|
| U2 | MC3373P | Motorola |
| U3 | NE555N | National |
| U4 | CD4017BE | National |
| D1 | MRD821 | Motorola |
| T1→T4 | IRF511 | International Rectifier El Segundo, CA |
| T5 | MPS222 | Motorola |
| P1→P4 | 8038EKP202 | MEPCO/Central Lab, Inc., Columbia, SC |
| R1 | 47 K Ω ¼W 5% Carbon Film | MEPCO |
| R2 | 1 K Ω ¼W 5% Carbon Film | MEPCO |
| R3 | 1 M Ω ¼W 5% Carbon Film | MEPCO |
| R4 | 10 K Ω ¼W 5% Carbon Film | MEPCO |
| R5 | 100 K Ω ¼W 5% Carbon Film | MEPCO |
| R6 | 1 M Ω ¼W 5% Carbon Film | MEPCO |
| R7 | 1 K Ω ¼W 5% Carbon Film | MEPCO |
| R8 | 3.3 K Ω ¼W 5% Carbon Film | MEPCO |
| R9 | 1 Ω 4W 1% RS-2B | Dale Electronics, Inc., Columbus, NE |
| C1 | 2*1.0 mF Elect. in Parallel 3476KG102M025JMBS | MEPCO |
| C2 | 220 μF Electrolytic 3476GD221M025JMBS | MEPCO |
| C3 | 220 μF Electrolytic 3476GD221M025JMBS | MEPCO |
| C4 | 10 μF Electrolytic 3476CB100M025JMBS | MEPCO |
| C5 | 0.1 μF Ceramic CW20C104K | MEPCO |
| C6 | 1.0 μF Electrolytic 3476CB109M050JMBS | MEPCO |
| C7 | 47 nF Ceramic CW20A473K | MEPCO |
| C8 | 47 nF Ceramic CW20A473K | MEPCO |
| C9 | 0.1 F Ceramic CW20C104K | MEPCO |
| C10 | 470 pF Ceramic CW15A471K | MEPCO |
| C11 | 10 F Electrolytic 3476CB100M025JMBS | MEPCO |
| C12 | 0.1 F Ceramic CW20C104K | MEPCO |

I claim:

1. A light generating apparatus for conducting vision testing, said apparatus comprising:
   an enclosure having at least one chamber with a face capable of transmitting light;
   an adjustable intensity light source within said chamber;
   sensing means positioned for sensing a parameter correlated to the sum of the intensity of the light generated by said light source and the intensity of ambient light incident upon said face; and
   control means connected to said light source and said sensing means, said control means providing an electrical energy input to said light source in response to said parameter to produce a substantially invariant level of illumination at said face notwithstanding changes in either the ambient illumination or the efficiency of said light source.

2. The apparatus of claim 1 wherein said control means is a variable power source.

3. The apparatus of claim 2 wherein said electrical energy input from said variable power source varies in direct relation to comparison of the voltage generated by said sensing means with a reference voltage.

4. The apparatus of claim 3 wherein said electrical energy input produces a predetermined output intensity from said light source.

5. The apparatus of claim 1 wherein said sensing means is located within said chamber.

6. The apparatus of claim 1 wherein a second sensing means is positioned in a second chamber in said enclosure, said second chamber with a face capable of transmitting light.

7. The light generating apparatus of claim 1 wherein said electrical energy input to said light source varies inversely with said light intensity in the vicinity of said sensing means.

8. The light generating apparatus of claim 1 wherein said sensing means is a photocell.

9. A light generating apparatus for conducting vision testing comprising:
- a plurality of chambers having faces capable of transmitting light;
- an adjustable intensity light source for each said chamber;
- at least one photocell positioned for sensing a parameter correlated to the sum of the intensity of the light generated by each said light source and the intensity of ambient light incident upon said faces;
- a switching circuit for directing an electrical energy input to a single said light source; and
- control means connected to said light sources, said photocell, and said switching circuit to provide said electrical energy input to said single light source in response to said parameter to produce a substantially invariant level of illumination at said faces.

10. The apparatus of claim 9 wherein said control means is a variable power source.

11. The apparatus of claim 9 wherein said electrical energy input from said variable power source varies in direct relation to comparison of the voltage generated by said photocell with a reference voltage.

12. The apparatus of claim 11 wherein said electrical energy input produces a predetermined output intensity from said light source.

13. The apparatus of claim 9 wherein said photocell is located within one of said chambers.

14. The apparatus of claim 13 wherein individual photocells are located within each said chamber.

15. The apparatus of claim 9 wherein said predetermined output intensity is adjustable.

16. The apparatus of claim 9 wherein said light source is at least one fluorescent bulb accepting an alternating current input at an amperage below about 20 mA.

17. The apparatus of claim 9 wherein said photocell has a range of sensitivity corresponding to that of the human eye.

18. The apparatus of claim 17 wherein said range is about 380 to about 700 nanometers.

19. The apparatus of claim 9 wherein said photocell has a cadmium sulfide sensor.

20. The light generating apparatus of claim 9 wherein said electrical energy input to said single light source varies inversely with said light intensity in the vicinity of said photocell.

21. A back-lit vision test apparatus comprising:
- an enclosure;
- a chamber within said enclosure having a face capable of transmitting light;
- an adjustable intensity light source within said chamber;
- a first photocell for detecting the light output of said light source;
- a second photocell for detecting ambient light distinct from said light output of said light source;
- control means connected to said light source and said first and second photocells to provide an electrical energy input to said light source correlated to the intensity of light detected by said first and second photocells to thereby produce a light intensity which creates a substantially invariant level of illumination at said face; and
- a light transmitting chart receivable on said face for presenting the vision test.

22. The apparatus of claim 21 wherein said control means is a variable power source.

23. The back-lit vision test apparatus of claim 21 wherein said electrical energy input to said light source varies inversely with said ambient light level.

24. A back-lit vision test apparatus comprising:
- an enclosure defining a plurality of chambers open at the front;
- a light source within each said chamber;
- a photocell within each said chamber;
- a light transmitting plate secured along said front of said chambers;
- a switching circuit for directing an electrical input to a single said light source;
- a variable power source connected to said light sources, said photocells, and said switching circuit to provide said electrical input to said single light source in response to the light intensity detected by said photocells in the vicinity of said photocells to thereby produce a predetermined output intensity which creates a substantially invariant level of illumination at said light transmitting plate; and
- a light transmitting chart securable on said plate for presenting the vision test.

25. The back-lit vision test apparatus of claim 24 wherein said electrical energy input to aid single light source varies inversely with said light intensity in the vicinity of said photocells.

* * * * *